United States Patent [19]

Nishimura et al.

[11] Patent Number: 4,996,200

[45] Date of Patent: Feb. 26, 1991

[54] USE OF ZN-PROTOPORPHYRIN FOR HEPATITIS TREATMENT

[75] Inventors: Yasuhiro Nishimura, Fujiidera; Motoko Suzuki, Ibaraki; Yozo Fukuda, Toyonaka, all of Japan

[73] Assignee: Hamair Chemicals, Ltd., Osaka, Japan

[21] Appl. No.: 423,700

[22] Filed: Oct. 18, 1989

Related U.S. Application Data

[63] Continuation of Ser. No. 150,397, Jan. 29, 1988, abandoned.

[30] Foreign Application Priority Data

Feb. 6, 1987 [JP] Japan ................................. 62-26776

[51] Int. Cl.$^5$ ..................... A61K 49/00; A61F 31/585
[52] U.S. Cl. ................................... 514/185; 514/894; 424/9
[58] Field of Search ................. 514/185, 894; 424/9

[56] References Cited

PUBLICATIONS

Qato et al.–Biochem. J. (1985), 226, 51–57.
Maines et al.–Biochem. J. (1984), 217, 409–417.
Maines–Biochimica Et Biophysica Acta, 673 (1981), 339–350.
"Bilirubin Metabolism and the Hereditary Hyperbilirubinemias", Paul D. Berk, Gastroenterology, vol. 5, 4th Edition, 1985, pp. 2732–2797.

*Primary Examiner*—Stanley J. Friedman
*Assistant Examiner*—Greg Hook
*Attorney, Agent, or Firm*—Burgess, Ryan & Wayne

[57] ABSTRACT

There is provided an oral antihepatopathic composition comprising protoporphyrin IX-Zn(II) complex. By oral administration, the complex can suppress the elevation of GPT and GOT as well as the increase of liver weight in a living body suffering from hepatic disorder, which contributes to prevention or relief of the disease.

4 Claims, No Drawings

USE OF ZN-PROTOPORPHYRIN FOR HEPATITIS TREATMENT

This application is a continuation, of application Ser. No. 150,397, filed 01/29/88.

The present invention relates to a novel antihepatopathic composition comprising protoporphyrin IX-zinc(II) complex as an active ingredient.

The liver, which is the largest single organ of the body, plays a central role in the metabolism in the body and its functions are widely varied, including the metabolism of various substances, detoxication, production of bilirubin, secretion of bile, and so on. These functions may be impaired, acutely or chronically, by various factors such as poisons, drugs, alcohol, viruses, malnutrition, radiation, cholestasis, and so on and such impairments are manifested as alcoholic liver disorder, viral hepatitis, drug-induced liver disease, hapatic disorder associated with cholestasis, fatty liver, jaundice and othe diseases. Where the impairments are long-sustained, hepatocirrhosis and even liver cancer may ensure. In treating these hepatopathies, repair of the injured liver tissue and improvement of the decreased function of the liver are acknowledged to be essential. However, in the absence of a satisfactory liver function-improving agent, the current therapeutic regimen consists basically of a diet therapy using high-calorie and high protein diets and rest treatment, and the administration of liver protecting drugs is superimposed thereon.

As a drug for this purpose, protoporphyrin disodium has been employed but no sufficient antihepatopathic effect can be expected of this drug. The use of immunopotentiators such as interferons has also been attempted but these drugs have the disadvantage that they cause strong side effects and that it takes a long time for their efficacies to be evaluated.

On the other hand, protoporphyrin IX-zinc(II) complex is a known compound and it is also known that the heme oxygenase activity of neotanal rat is inhibited by subcutaneous or intraperitoneal administration [Biochimica et Biophysica Acta, 673 (1981) pp 339-350; Biochem. J. (1985) 226, pp 51-57; ibid. (1984) 217, pp 409-417].

Furthermore, it is suggested that bilirubin formation and heme activity in mammalians are suppressed by subcutaneous or intravenous injection [Clin. Pharmacol. Ther., Vol. 39, pp 510-520 (1986)].

However, the hepatopathy-suppressing activity of protoporphyrin IX-zinc(II) complex in oral administration has not been revealed at all until now.

The present inventors have explored the possibility of developing a drug which would be free of the above-mentioned disadvantages and have potent antihepatopathic action by oral administration.

Hepatopathy or liver disorder is epitomized by several characteristic clinical, biochemical, and histological findings such as elevation of hapatic enzymes in the blood, such as glutamic-pyruvic transaminase (GPT), glutamic-oxaloacetic transaminase (GOT), and alkaline phosphatase, elevation of serum bilirubin, necrosis of hepatocytes, and so on. Elevation of serum GPT and GOT levels are observed in all hepatic disorder in common and the determination of such hepatic enzyme activities and bilirubin levels in the blood has been utilized in the charaterization of hepatopathy and evaluation of its severity and is routinely used in clinical laboratory test. Therefore, the screening of prophylactic and therapeutic agents for hepatic disorder is usually conducted utilizing these parameters.

For the experimental study of hepatic disorder, a variety of hepatitis models have been developed. Among them, models in rats or mice suffering from hepatic disorder induced by carbon tetrachloride are frequently utilized. Hepatic disorder induced by carbon tetrachloride has been considered to be caused as the administered carbon tetrachloride is transformed into the free radical ($°CCl_3$) by cytochrome P-450 within the liver cell and this free radical is bound to the cell membrane protein of hepatocytes to strongly inhibit the cellular activity or stimulates the peroxydation reaction of the membrane lipid of its organelle, which results in alterations in the membrane structure, thus damaging the hepatocytes.

Using model animals suffering from hepatic disorder induced by carbon tetrachloride, the present inventors tested various porphyrin derivatives and found that protoporphyrin IX-zinc(II) complex definitely inhibits the elevation of GPT and GOT in the blood and also inhibits increase of liver weight, exhibiting a potent ameliorating effect on the hepatic disorder.

Predicated on the above findings, one aspect of the present invention is directed to an antihepatopathic composition for oral administration which comprises protoporphyrin IX-Zn(II) complex in an effective amount for suppressing the increases of glutamic-oxaloacetic transaminase and glutamic-pyruvic transaminase in serum, and a carrier.

A further aspect of the invention is directed to a method for suppressing the increases of glutamic-oxaloacetic transaminase and glutamic-pyruvic transaminase in serum, which comprises administering orally an effective amount of protoporphyrin IX-Zn(II) complex to a mammalian.

Protoporphyrin IX-zinc(II) complex according to the invention can be easily synthesized from protoporphyrin IX by the known method.

In the present invention, protoporphyrin IX-zinc(II) complex is administered orally. For the administration, it can be provided in such dosage forms as powders, tablets, pills, capsules, granules, suspensions, and so on.

The complex may be administered to a patient in a dosage of 10 milligrams to 5 grams per day and preferably 10 milligrams to 1 gram, however, this dosage may be decreased or increased according to the condition of the patient. If desired, the complex may be administered with other drugs.

Thus, the present invention provides an oral drug which improves hepatic functions and suppresses hepatic disorder, facilitating the prevention and treatment of hepatopathy which has heretofore been difficult to manage.

The following examples and reference examples are intended to illustrate the present invention, employing mice as a model of mammalians, in further detail and should by no means construed as limiting the scope of the invention.

EXAMPLE 1

Method

Male ICR mice aged 4 weeks were used in groups of 10 animals. The test substance was suspended in 4% aqueous gum arabic solution and the suspension was administered by oral gavage once a day for 7 consecutive days. Concurrently with the last administration, carbon tetrachloride in 25% olive oil was administered subcutaneously in a volume of 2 ml/kg (0.5 ml/kg as carbon tetrachloride). The animals were then deprived of food for 24 hours, at the end of which time the blood was drawn from the abdominal aorta under ether anesthesia. The blood was centrifuged (3,000 r.p.m., 15 minutes) to separate the serum and GPT and GOT activities in the serum were determined (Reitmann-Frankel's method). In addition, the liver was excised and weighed.

To the control group, 4% aqueous gum arabic solution was orally administered for 7 days and carbon tetrachloride-olive oil was subcutaneously administered. To the normal group, 4% aqueous gum arabic solution was orally administered for 7 days and olive oil alone was subcutaneously administered. As the control drug, malotilate was used.

The results are shown below in the table.

| Group | Dosage (mg/kg) | GOT (KU) | GPT (KU) | Liver weight |
|---|---|---|---|---|
| Normal | | 119 ± 24 | 25 ± 3 | 1.05 ± 0.03 |
| Control | | 5606 ± 887 | 6661 ± 774 | 1.40 ± 0.03 |
| Zn-PP | 20 | 3520 ± 653 | 3175 ± 358*** | 1.39 ± 0.03 |
| | 100 | 2970 ± 551* | 1970 ± 172*** | 1.29 ± 0.04* |
| Malotilate | 100 | 3245 ± 552* | 4263 ± 320* | 1.39 ± 0.04 |

Note
*$P < 0.05$,
***$P < 0.001$
KU: Karmen unit (the same applies to the following tables)
Zn-pp: Protoporphyrin IX-Zn(II) complex According to the above results, protoporphyrin IX-Zn(II) complex of the present invention dose-dependently inhibited the elevation of serum GPT and GOT and also inhibited the increase of liver weight. Furthermore, the administration of the drug at 100 mg/kg caused significant decreases in GPT, GOT and liver weight. It was thus made clear that the drug prevents carbon tetrachloride-induced hepatic disorder.

REFERENCE EXAMPLE 1

The test procedure of Example 1 was repeated except that protoporphyrin IX-Sn(IV) complex was used as the test substance. The results are shown in the following table.

| Group | Dosage (mg/kg) | GOT (KU) | GPT (KU) | Liver weight |
|---|---|---|---|---|
| Normal | | 62 ± 3 | 28 ± 6 | 0.90 ± 0.03 |
| Control | | 2723 ± 483 | 6364 ± 944 | 1.17 ± 0.04 |
| Sn-PP | 20 | 2839 ± 398 | 7322 ± 1060 | 1.23 ± 0.03 |
| | 100 | 2489 ± 222 | 6500 ± 477 | 1.26 ± 0.04 |

Note
Sn-pp: Protoporphyrin IX-Sn(IV) complex

The above results indicate that protoporphyrin IX-Sn(IV) complex has no prophylactic effect on carbon tetrachloride-induced hepatic disorder.

REFERENCE EXAMPLE 2

The test procedure of Example 1 was repeated except that protoporphyn disodium was used as the test substance. The results are shown in the following table.

| Group | Dosage (mg/kg) | GOT (KU) | GPT (KU) | Liver weight |
|---|---|---|---|---|
| Normal | | 51 ± 4 | 28 ± 2 | 0.96 ± 0.05 |
| Control | | 4771 ± 726 | 10958 ± 1866 | 1.37 ± 0.05 |
| PPN | 20 | 3825 ± 836 | 9400 ± 2287 | 1.30 ± 0.04 |
| | 100 | 3565 ± 484 | 8415 ± 772 | 1.36 ± 0.05 |
| | 500 | 3029 ± 713 | 9200 ± 1748 | 1.37 ± 0.06 |

Note
PPN: Protoporphyrin disodium

The above results indicate that protoporphyn disodium has little prophylactic effect on carbon tetrachloride-induced hepatic disorder.

The protoporphyrin compounds employed in the above examples are prepared as shown in the following:

REFERENCE EXAMPLE 3

Protoporphyrin IX-Zn(II) complex:

Protoporphyrin IX dimethyl ester (1.1g) was dissolved in methylene chloride (200 ml). The solution was refluxed gently, a saturated solution of zinc acetate in methanol (50 ml) was added thereto and refluxed for further 2 hours. After it was allowed to come to room temperature, the mixture was washed three times each with 200 ml of water and dried over anhydrous magnesium sulfate, and then solvent was removed from the mixture by distillation. The residue was subjected to alumina column chromatography employing chloroform as an eluant to obtain red fraction. Solvent was removed from the fraction by distillation and the remaining residue was recrystallized from the mixed solvent of methylene chloride and methanol to obtain 800 mg of protoporphyrin IX dimethylester-Zn(II) complex as reddish purple crystals.

The crystals were dissolved in pyridine (250 ml), 1 N aqueous sodium hydroxide solution (16 ml) was added thereto, and the mixture was refluxed for 2 hours. After the mixture was allowed to come to room temperature, solvent was removed from the mixture by distillation and the resulting residue was dissolved by adding water (50 ml) thereto. To the solution, a suitable amount of acetic acid was added, and resulting precipitates were collected by filtration, washed with water and dried to obtain 560 mg of protoporphyrin IX-Zn(II) complex as dark red crystals.

Electronic spectrum ($\gamma_{max}{}^{nm}$, DMF): 419.8, 547, 584.2

IR (KBr, $cm^{-1}$): 3450, 2910, 1710.

NMR (DMF−$d_7$, δ ppm): 3.31 (t, 3H), 3.64 (s, 3H), 3.65 (s, 3H), 3.78 (s, 6H), 4.44 (t, 3H), 6.25 (dd, 2H), 8.53 (dd, 1H), 10.22 (s, 1H), 10.25 (s, 2H), 10.33 (s, 1H).

Protoporphyrin IX-Sn(IV) complex:

Protoporphyrin IX dimethyl ester (100 mg) was dissolved in methylene chloride (100 ml) and the solution was refluxed gently. To the solution, a saturated solution of tin(II) actate in methanol (20 ml) was added gradually and the mixture was refluxed for further 2 hours. After it was allowed to come to room temperature, the mixture was washed three times with each 100 ml of water and fried over anhydrous magnesium sulfate. Then, solvent was removed from the mixture by distillation and the residue was purified by alumina (Merck, active grade II-III) column chromatography to obtain 80 mg of protoporphyrin dimethyl ester-Sn(IV) complex.

The complex was dissolved in a solution of potassium hydroxide (100 mg) in methanol, a small amount of water was added thereto and the mixed solution was refluxed for 2 hours. The resulting residue was dissolved by the addition of water (10 ml) and acetic acid (0.1 ml) was added to the solution.

Resultant precipitates were collected by filtration, washed with water and dried to obtain 65 mg of protoporphyrin IX-Sn(IV) complex.

Electronic spectrum ($\gamma_{max}^{nm}$, DMF): 416.5, 546, 584.5.

IR (KBr, cm$^{-1}$): 3450, 2910, 2850, 1705.

NMR ($\delta$ppm, CF$_3$COOD): 12.3 (s, 1H), 12.1 (s, 1H), 11.7 (s, 2H), 9.33 (dd, 2H), 7.23 (dd, 4H), 5.30 (br.t, 4H), 4.33 (br.s, 12H), 4.03 (br.t, 4H).

What is claimed is:

1. A method for suppressing the increase of glutamic-oxaloacetic transaminase and glutamic-pyruvic transaminase in the serum of a patient suffering from hepatitis, which comprises administering orally a therapeutically effective amount of protoporphyrin IX-Zn(II) complex to said patient exhibiting said elevated levels of glutamic-oxaloacetic transaminase and glutamic-pyruvic transaminase in said serum.

2. A method according to claim 1, wherein protoporphyrin IX-Zn(II) complex is administered in a form of powder, tablets, pills, capsules or granules or suspensions.

3. A method according to claim 1, wherein a daily does of 10 mg to 5 g, is administered to the patient.

4. A method according to claim 1 wherein a daily dose of 10 mg to 1 g, is administered to the patient.

* * * * *

UNITED STATES PATENT AND TRADEMARK OFFICE
CERTIFICATE OF CORRECTION

PATENT NO. : 4,996,200

DATED : February 26, 1991

INVENTOR(S) : Yasuhiro Nishimura, et al

It is certified that error appears in the above-identified patent and that said Letters Patent is hereby corrected as shown below:

On the title page:

Item 73: Please correct the spelling of the Assignee from: "Hamair Chemicals, Ltd., Osaka, Japan"

to: --Hamari Chemicals, Ltd., Osaka, Japan--

Signed and Sealed this

Seventeenth Day of November, 1992

Attest:

DOUGLAS B. COMER

Attesting Officer

Acting Commissioner of Patents and Trademarks